(12) United States Patent
Lampela

(10) Patent No.: US 7,204,914 B2
(45) Date of Patent: Apr. 17, 2007

(54) SYSTEM AND METHOD FOR CONTROLLING A PROCESSOR INCLUDING A DIGESTER UTILIZING TIME-BASED ASSESSMENTS

(75) Inventor: Kari Juhani Lampela, Duluth, GA (US)

(73) Assignee: Metso Automation USA Inc., Norcross, GA (US)

( * ) Notice: Subject to any disclaimer, the term of this patent is extended or adjusted under 35 U.S.C. 154(b) by 0 days.

(21) Appl. No.: 10/639,509

(22) Filed: Aug. 13, 2003

(65) Prior Publication Data

US 2005/0034824 A1   Feb. 17, 2005

(51) Int. Cl.
   *D21C 7/12*   (2006.01)

(52) U.S. Cl. .................. 162/238; 162/198; 162/62; 162/49; 162/DIG. 10; 162/262; 162/263; 700/127; 700/128; 700/129; 700/29

(58) Field of Classification Search ........... 162/238, 162/62, 49, DIG. 10, 198, 262–263; 700/29, 700/127, 128, 129; 364/150, 137
   See application file for complete search history.

(56) References Cited

U.S. PATENT DOCUMENTS

| | | | |
|---|---|---|---|
| 4,216,054 A | 8/1980 | Bentvelzen et al. | |
| 5,032,977 A | 7/1991 | Beller et al. | |
| 6,421,575 B1 * | 7/2002 | Shakespeare | ............... 700/127 |

OTHER PUBLICATIONS

TAPPI Test Methods, 1996-1997, TAPPI Press, 1996, T 236 cm-85, pp. 1-3.

* cited by examiner

*Primary Examiner*—Mark Halpern
(74) *Attorney, Agent, or Firm*—Oblon, Spivak, McClelland, Maier & Neustadt, P.C.

(57) ABSTRACT

A system for controlling a processor having at least one sampling port connected to a stage of the processor in order to sample a reactant product from the processor. The system includes a controller configured to control a processing parameter of the processor based on measurements of at least one property of the reactant product such that changes to the processing parameter maintain a target value for the at least one property of the reactant product. The system further includes a dead time compensator. The dead time compensator is configured, based upon a prescribed dead time related to a time before at least one effect of at least one change to the processing parameter is fully realized, to evaluate the reactant product to determine if the effect has been realized at a plurality of sequential times offset from the dead time.

27 Claims, 8 Drawing Sheets

| Blow Kappa Error | Residual Alkali Error | H-factor Correction | Alkali Dosage Correction |
|---|---|---|---|
| High | High | + + | OK |
| High | OK | + | + |
| High | Low | OK | + + |
| OK | High | + | - |
| OK | OK | OK | OK |
| OK | Low | - | + |
| Low | High | OK | - - |
| Low | OK | - | - |
| Low | Low | - - | OK |

| Blow Kappa Error | Residual Alkali Error (% of $Na_2O$) | H-factor Correction | Alkali Dosage Correction (% $Na_2O$) |
|---|---|---|---|
| + 2 | 0.05 | 100 | 0 |
| + 2 | 0 | 50 | 0.25 |
| + 2 | -0.05 | 0 | 0.5 |
| 0 | 0.05 | 50 | -0.25 |
| 0 | 0 | 0 | 0 |
| 0 | -0.05 | - 50 | 0.25 |
| - 2 | 0.05 | 0 | -0.5 |
| - 2 | 0 | - 50 | -0.25 |
| - 2 | -0.05 | -100 | 0 |

FIGURE 8

SYSTEM AND METHOD FOR CONTROLLING A PROCESSOR INCLUDING A DIGESTER UTILIZING TIME-BASED ASSESSMENTS

DISCUSSION OF THE BACKGROUND

1. Field of the Invention

This invention relates to the control of processes and processing equipment, and in particular production processes/equipment for use in the pulp and paper industry. The invention is particularly advantageous for pulp digesters.

2. Background of the Invention

Processors storing large quantities of chemically reactive (and some cases reacting) fluids are utilized extensively throughout the paper and pulp industry. Typically, the processes and equipment are "in-line" with the output from one processor providing the input to a subsequent downstream processor. Each processor in the paper and pulp industry processes a large tonnage of product. For example, a continuous digester, can process more than 1,300 tons per day of digested pulp. Output from a pulp digester becomes input to downstream processors such as for example oxygen delignification processors, bleaching processors, and causticizers.

FIG. 1 is a schematic diagram depicting a number of in-line processing units processing raw pulp products toward a final output product suitable for paper production. FIG. 1 shows specifically a chemical pulp manufacturing process flowing from left to right with output from a digester 2 flowing to an oxygen delignification processor 4 and then to a bleaching processor 6. The spent liquid effluent extracted from the digester 2 is feed "off-line" to a causticizer 8 which restores the spent liquid effluent to a proper alkali concentration before return to the digester 2. The causticizer 8 itself represents another processor (e.g. a vat processor containing large quantities of chemically reactive fluids whose output product must be controlled to a desired standard in the manufacturing line). With this type of arrangement or system, deviations from target specifications of the resultant product from any one stage can impact the downstream processors.

Continuous pulp digesters are very complex vertical reactors (typically tubular) used in the pulp and paper industry to remove lignin from wood chips. Usually, continuous digesters are separated into multiple reaction and extraction zones. Optimal control of a digester can be difficult due to long dead times in which changes to input process variables are not immediately apparent. When a process parameter is changed or a step commences, e.g., by the addition of a material such as an alkali or by affecting a temperature change, the end effect is not immediately apparent due, e.g., the time required to realize the effect and the inertia of the system. The time from when a change occurs to the point at which the effect is realized, fully or partially, can be referred to as "dead time."

In order to yield large or more optimum production quantities of digested product and to be economical with a minimum of chemicals and energy usage, the process must be controlled to maintain optimum cooking conditions throughout the digester to ensure selective delignification while simultaneously optimizing pulp quality and production costs. To facilitate control, reliable pulp quality measurements are often used to provide accurate real-time information. Indeed, certain basic control and quality measurements—Kappa, pulp strength, and chemical residuals—have been made regularly for decades. In the past, analyses of these properties were made off-line in the laboratory, but such analyses were slow and error-prone. However, with recent advances in measuring technologies, these analyses have been extensively automated such that measurements can be made on-line. To maximize the impact of automated measurements, there is a need for efficient controls and/or control methods that are easy to modify, tune, and configure, and yet can handle the complexity of continuous digester processes.

As a consequence of the heterogeneities in the feedstock, i.e. the wood pulp, a digester undergoes constant changes due to the complicated structure and properties of the various wood pulps being fed to the digester. Besides differences in the pulp feedstock from one particular batch of wood chips to another, even the moisture content of the chips being fed into the digester can vary by as much 30% during a single day's production. Further, the large amounts of wood pulp and chemicals contained in the digester create a "chemical inertia" which makes instantaneous changes to the digesting conditions, such as for example changes in alkali concentration, cooking temperature, and white liquor concentration, difficult if not impossible to rapidly adjust. As a consequence, it is generally impossible to describe the dynamics of digester with precise mathematical models. Furthermore, a typical retention time for the pulp in a digester can in some cases exceed five hours. Due to possible channeling (i.e., unexpected changes in plug flow in the tubular reactor) or other unexpected disturbances, it is impossible to estimate the retention time accurately for a particular pulp product flowing through the digester.

As noted, a digester can process more than 1,300 tons per day of digested pulp. Maximizing pulp production at a specified Kappa number using a minimum input of chemicals and energy and a minimal waste discharge is highly desirable in order to produce an efficient pulp digesting process. In a digester, lignin is removed from for example wood chips. Lignin is the naturally occurring bonder in a wood product which bonds the wood fibers together. An aqueous solution of the sodium hydroxide and hydrosulfide (i.e., white liquor) is used to react (i.e., to digest) the wood products inside the digesters thereby dissolving the lignin from the wood product.

Presently, a titration method is a known and commonly used to measure a Kappa number of various pulps. This titration method is described in Tappi Test Methods—T236 cm-85, Tappi Press, 1996, the entire contents of which are incorporated herein by reference. Using the titration method, a pulp Kappa number is calculated using the difference between the initial volume of potassium permanganate blank solution and the final volume of potassium permanganate remaining after oxidation of lignin in the pulp-permanganate solution. For example, the digestion of wood chips in an alkali solution and the resulting pulp Kappa number obtained using a permanganate solution are both described in Bentvelzen et al. (U.S. Pat. No. 4,216,054), the entire contents of which are incorporated herein by reference. Kappa number is not the only one way to measure lignin, e.g. others like K-number, P-number and others known in the art can be used.

Prior to entry into the digester, wood chips are typically cooked and steamed (to remove air from the pores of the chips) and fed into an impregnation vessel together with the white liquor. While in the impregnation vessel, white liquor penetrates the chips, and the chips are subsequently carried into a top section of the digester where a mixture of the wood chips and the white liquor is brought to a desired reaction temperature. In a top section of the digester, the chips react with the white liquor to digest the lignin, and spent liquor (i.e., that liquor which has been depleted of its alkalinity by the chemical reaction with the lignin) is extracted as the digested chips migrate into lower cooking sections. Fresh white liquor is added to further continue the delignification process. The blow Kappa number of the digested (i.e., reacted) product can be assessed from a blow-line (i.e., an exit line) in which the Kappa number provides a measure of how effectively the lignin has been digested from the wood fiber.

As disclosed for example in Beller et al. (U.S. Pat. No. 5,032,977), the entire contents of which are incorporated herein by reference, to address the complexities of controlling a wood digester, "model" based control processes have been developed. In a model-based control process, a model assumes the input properties of the pulp product entering the digester, calculates expected values for the resultant properties of the digested product, and alters the process variables of the reactor (e.g., the pulp product feed rate, the alkali input feed, and the digester temperature) to affect the resultant properties. A model based approach is a complex approach requiring complicated calculations if any kind of reliable prediction of the reactor is to be made. Yet, for the above-noted reasons, pulp digesters are not simple chemical fluid beds conducive to model based predictions. Initial assumptions of input properties and the resulting models of the digester are susceptible to variations of the input properties and are susceptible to unexpected changes in the product flow through the large digester (i.e., the above-noted channeling). When unexpected changes occur, model based controls have no way to recognize that the unexpected changes may be spurious. The model based controls consequently improperly compensate the input process variables, thus producing control oscillations and instabilities in the output properties of the digested wood product.

While model based controls, such as those described by Beller et al. for example, can use adaptive control to learn and refine the process control model, the learning process needs to be based on at least a quasi-steady state condition maintained in the reactor. Otherwise, what is learned is in error. Indeed, in those models which use adaptive control, a disturbance to the steady state operation can result in the models being temporarily skewed, as the "learned" refinements are not representative of the process when unexpected disturbances occur. As a result, when unexpected disturbances occur, once again a series of oscillations in the model-based control occurs, producing process control instability.

The problems illustrated above for a pulp digester extend to other paper mill processes listed above such as for example the oxygen delignification processors, the bleaching processors, and the causticizers, and in general are prevalent in any chemical processor in which imhomogeneities in input feedstock, the chemical inertia of the process reactor, and/or the fluid flow make problematic the accurate prediction of future changes following changes to input parameters.

SUMMARY OF THE INVENTION

Consequently, there exists a need for an improved system and method for controlling processing equipment, particularly processing equipment used in the pulp and pager industry. Particularly needed is a system and method for minimizing or avoiding instabilities which can result from disturbances or changes to the processors or process conditions.

Thus, one object of the present invention is to provide a control which reduces the impact of disturbances on the quality and production of a processor.

Yet, another object of the present invention is not to utilize model-based control in which process models or detailed process knowledge are required for tuning and control. For example, processors in the pulp and paper mill industry represent applications where a complex predictive model, for example a neural network based control, would not be an accepted practice as the pulp and paper mill industry can not afford to risk the production of more than 1,300 tons per day of digested pulp on complex software installed on a processor controls which can not be routinely upgraded, routinely monitored, and installed on site.

A further object of the present invention is to a provide a control in which long-term disturbances on processors are minimized.

Yet another object of the present invention is to provide a control for pulp digesters and other paper mill processors such as for example oxygen delignification processors, bleaching processors, and causticizers.

Still, a further object of the present invention is to provide a control in which exact knowledge of dead times (i.e., those times after a process change is implemented and before the results are fully realized) are not needed for stable process control. As such, in one aspect of the present invention, a tunable time "window" is utilized to see if the processor in responding to a process change matches the resultant change to an expected change and consequently to a target value for an output property of the reacted product.

These and other objects are accomplished, according to the present invention. In accordance with an exemplary embodiment, a system for controlling a processor is provided having at least one sampling port connected to a stage of the processor to sample a reactant product from the processor. The system includes a controller configured to control a processing parameter of the processor based on measurements of at least one property of the reactant product such that changes to the processing parameter maintain a target value for the at least one property of the reactant product. The system further includes a dead time compensator. The dead time compensator is configured, based upon a prescribed dead time related to a time before at least one effect of at least one change to the processing parameter is fully realized, to evaluate the reactant product to determine if the effect has been realized at a plurality of sequential times offset from the dead time.

According to an exemplary method of the present invention, a reactant product from the processor is analyzed to determine, based on at least one property of the reactant product, a charge to at least one processing parameter. The processing parameter(s) is/are changed, and, following a prescribed process dead time, changes to the at least one property of the reactant is evaluated at a number of times/time intervals as the effects of the change(s) become realized. By way of example, according to a preferred method, a "dead time" can be estimated during which the effects of the change(s) will not be expected to have been fully realized. After this selected or predetermined dead time, one or more properties of the reactant are evaluated at plural different times/time intervals to determine the magnitude and timing of the effects of the process parameter change(s).

BRIEF DESCRIPTION OF THE DRAWINGS

A more complete appreciation of the present invention and many of the attendant advantages thereof will be readily obtained as the same becomes better understood by reference to the following detailed description when considered in connection with the accompanying drawings, wherein:

FIG. 8 is a depiction of bifurcated control data according to one aspect of the invention.

DETAILED DESCRIPTION OF THE PREFERRED EMBODIMENTS

Figure 1:
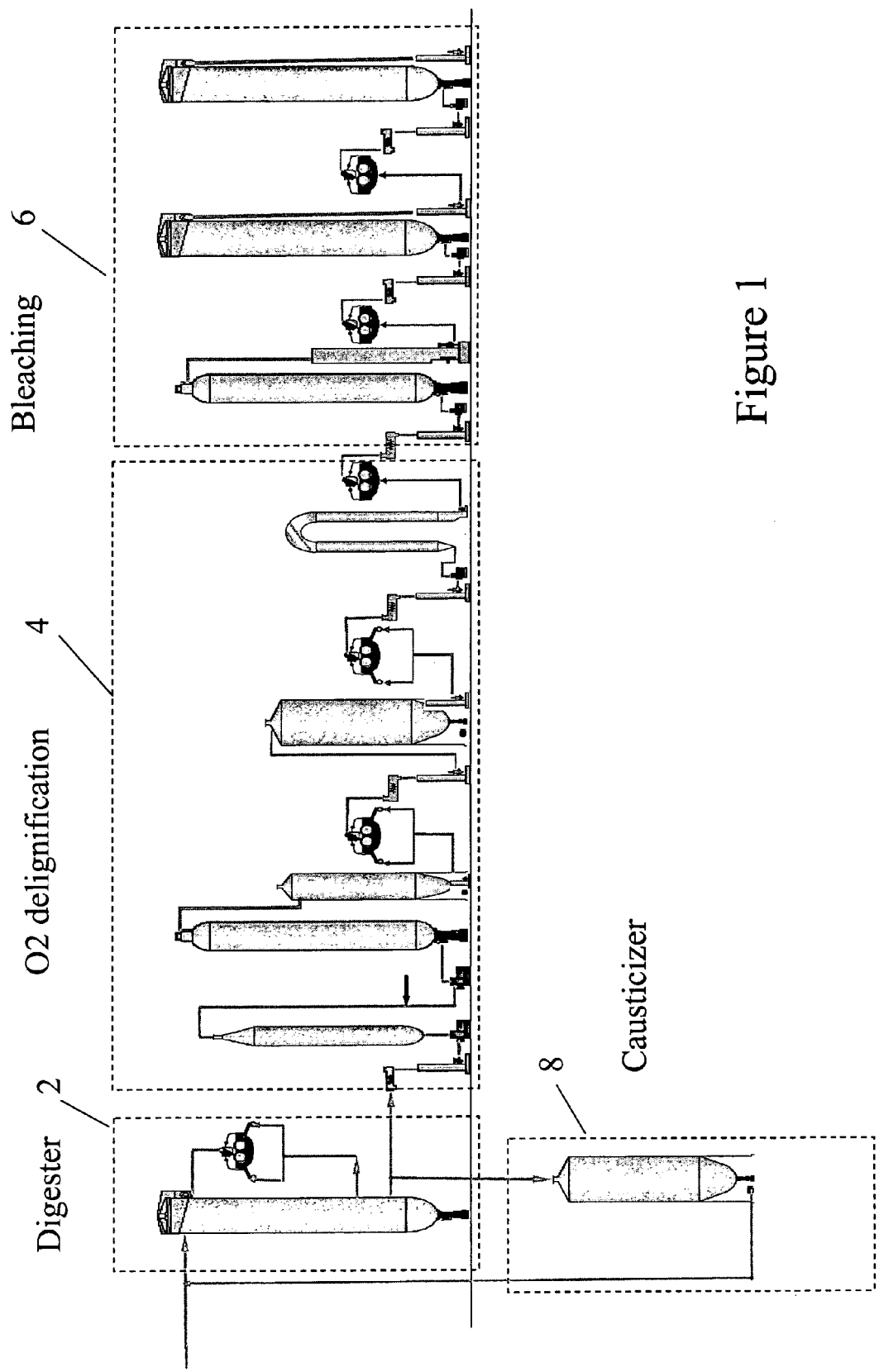
FIG. 1 is a schematic of a generic manufacturing line in a pulp plant.
Figure 2:
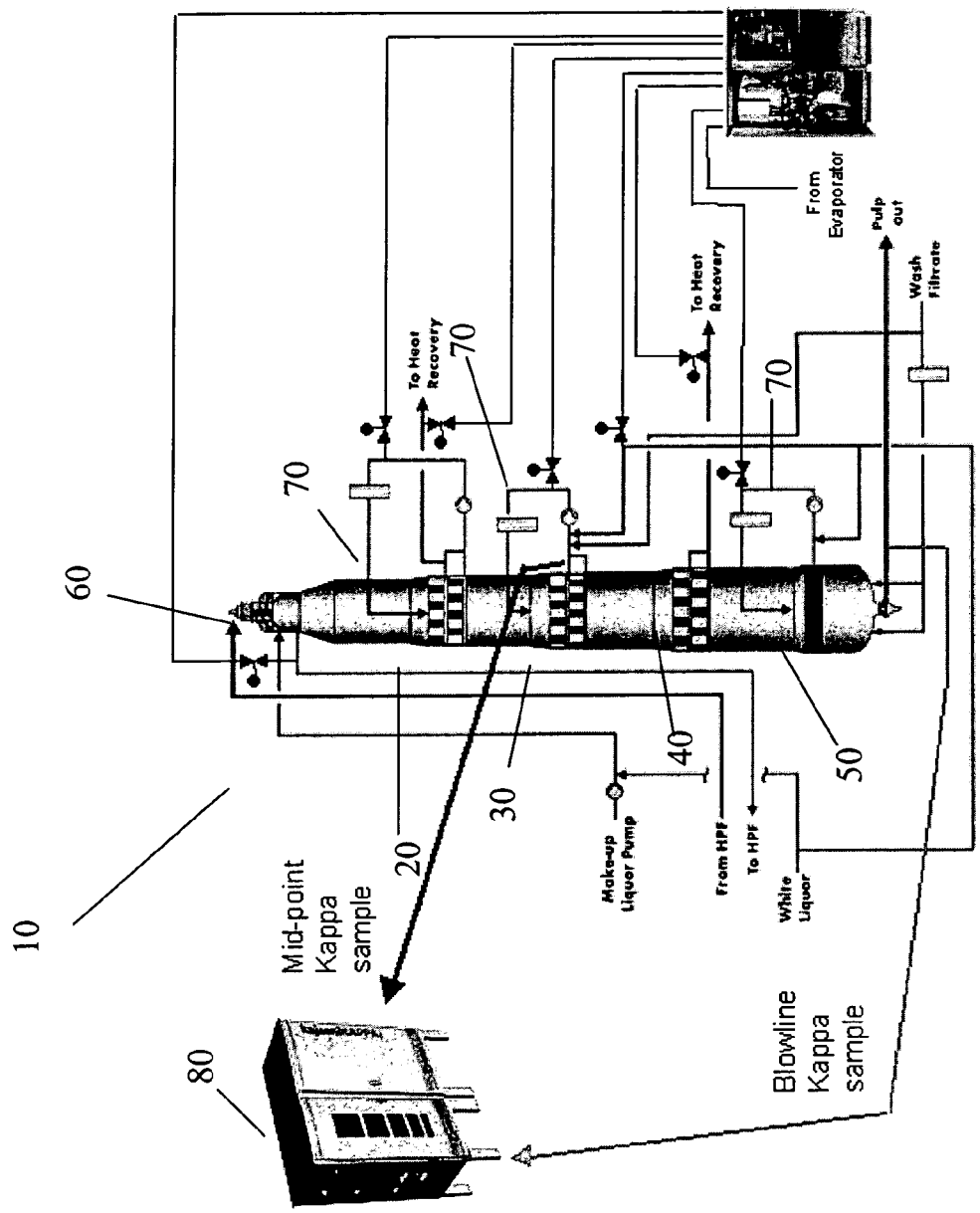
FIG. 2 is a schematic of a system for a processor including a controller according to the present invention.

Referring now to the drawings, wherein like reference numerals designate identical or corresponding parts throughout the several views, and more particularly to FIG. 2 thereof, FIG. 2 is a schematic diagram of a processor including a controller 80 according to the present invention. The processor in FIG. 2 is schematically represented as a pulp digester 10, but could equally well typify other pulp mill processes such as for example the oxygen delignifcation processors, the bleaching processors, and the causticizers mentioned above in which reactant products from the processes are monitored to provide control.

As shown illustratively in FIG. 2, a pulp digester 10 of the present invention includes sequential cooking sections illustrated here by an upper cooking section 20, a mid-cooking section 30, an extended-cooking section 40, and a discharge section 50. White liquor, including for example the aforementioned sodium hydroxide and hydrosulfide, is introduced into the pulp digester 10 by inlet 60 located at the top of the pulp digester 10. Also introduced by way of the inlet 60 is an input pulp product which mixes with the white liquor in the upper cooking section 20 of the pulp digester 10. Attached to the pulp digester 10 can be a number of sampling loops 70 which permit extraction of chemically-spent white liquor and the reacted pulp product from the pulp digester.

The extracted fluid can be used to measure alkali content or a representative Kappa number of the digested pulp product at whatever section 20, 30, 40, and/or 50 where the liquid is extracted. A blow Kappa number and likewise a residual alkali concentration taken from the discharge (i.e., blow) section 50 of the pulp digester are pertinent production targets for control of the digester.

In a digester, there are a number of ways to influence the blow Kappa level. For example, either the temperature or the alkali level can be changed. The temperature control is typically adjusted through adjustments of an H-factor. The H-factor is a calculated (i.e. integrated) factor which, as described in Beller et al., is a time-integration of the delignification reaction rate constant k in an Arrhenius rate equation. The H-factor thus captures numerically a value indicative of a pulp product time and temperature as the pulp product flows temporally through the entirety of the digester. When an input alkali level is increased, the blow Kappa number (representing the residual amount of lignin in the pulp product) typically decreases, and at the same time the residual alkali typically increases. On the other hand, when the digester temperature is increased, the blow Kappa number is typically again decreased, but the residual alkali also decreases due to faster chemical reaction rates owing to the increased temperature. Thus, the control of the present invention analyzes jointly the blow Kappa number and the residual alkali to determine that the blow Kappa number and the residual alkali are within targeted and/or expected values. Upon recognizing an error, the control according to the present invention selects, based on composite errors from a target blow Kappa number and target residual alkali, appropriate adjustments for example to the H-factor and the alkali dosage concentrations accordingly. Alternatively, adjustments to an alkali/wood-input ratio to the digester can be utilized instead of a strict increase in the input alkali dosage concentration (e.g., the input pulp or paper product feed rate could be reduced while maintaining the same input alkali feed rate).

Table 1 shown below depicts a generic rule base according to the present invention used, for example by a pulp digester, to select a response based on a composite error realized in the blow Kappa number and the residual alkali. As can be seen from an analysis of the generic rule base, the errors in blow Kappa and residual alkali from target values are categorized into three states ("high", "ok", and "low"). For two variables and three states, there exist nine possible processor states to which rules for each of these states are prescribed. For these nine states, there are measured responses for changes to the input process variables. From the measured responses, appropriate corrections denoted as "++", "+", "--", and "-" are implemented, where blow Kappa error is representative of an error from an expected cellulose fiber concentration in a discharge section of the digester, residual alkali error is representative of an error from an expected residual alkali concentration, H-factor correction is based on a time-integrated rate constant for the pulp or paper product in the digester based on a temperature and a throughput of the digester, alkali dosage correction is based on a measured addition of alkali to be added to the digester, + and ++ indicate an increase and a stronger increase to the corrections, and - and -- indicate a decrease and a stronger decrease to the corrections. "OK" refers to an expected value of the residual alkali concentration or the expected cellulose fiber concentration. "High" refers to deviations above the expected values which are predetermined to exceed process tolerances and typically for pulp processors is marked by a deviation of more than 0.05% above the expected values. "Low" refers to deviations below the expected values which are predetermined to be below process tolerances and typically for pulp processors is marked by a deviation of more than 0.05% below the expected values.

When the alkali level is increased, the blow Kappa number decreases and at the same time the residual alkali increases. On the other hand, when the temperature is increased, the blow Kappa is again decreased, but now the residual alkali decreases. The control incorporates the residual alkali and blow Kappa to same control algorithm to keep the blow Kappa and residual alkali level both within respective targets.

TABLE 1

| Blow Kappa Error | Residual Alkali Error | H-factor Correction | Alkali Dosage Correction |
|---|---|---|---|
| High | High | ++ | OK |
| High | OK | + | + |
| High | Low | OK | ++ |
| OK | High | + | − |
| OK | OK | OK | OK |
| OK | Low | − | + |
| Low | High | OK | −− |
| Low | OK | − | − |
| Low | Low | −− | OK |

Some of these changes appear to contradict a simple linear response, as might be used in a proportional control. For example, the first row of Table 1 indicates the presence of a "High" error for both the blow Kappa number and the output residual alkali. Normally, in proportionate controls, one would correspondingly adjust both the H-factor and the alkali dosage to compensate. Yet, as illustrated here, the rules only require increasing only the H-factor when both the blow Kappa number and the output residual alkali are "High" to properly control the pulp digestion to maintain digested pulp production without excessive use of alkali The rule base recognizes that to perform both a H factor and an alkali dosage correction would have resulted in the digester depleting the alkali, generating incomplete digestion and forcing another round of corrective actions.

Table 2, shown below, is an example of a specific rule base according to the present invention, used by a pulp digester, to select a response based on a composite error realized in the blow Kappa number and the output residual alkali.

TABLE 2

| Blow Kappa Error | Residual Alkali Error (% of Na$_2$O) | H-factor Correction | Alkali Dosage Correction (% Na$_2$O) |
|---|---|---|---|
| +2 | 0.05 | 100 | 0 |
| +2 | 0 | 50 | 0.25 |
| +2 | −0.05 | 0 | 0.5 |
| 0 | 0.05 | 50 | −0.25 |
| 0 | 0 | 0 | 0 |
| 0 | −0.05 | −50 | 0.25 |
| −2 | 0.05 | 0 | −0.5 |
| −2 | 0 | −50 | −0.25 |
| −2 | −0.05 | −100 | 0 |

In this exemplary table, consider a processor (e.g., a pulp digester) operating with a caustic/wood weight percentage of 18%. A correction in the processor Na$_2$O concentration of 0.25, as given for example in the second rule, would correspond to a change in the processor percentage concentration of Na$_2$O from 18% to 18.25%.

According to the present invention, values for H-factor and alkali dosage concentrations are adjusted according to linear interpolations of the H-factor and alkali dosage concentrations based on respective proportionate errors in the blow Kappa and the residual alkali. Thus, in one embodiment of the present invention, the digester is controlled such that both the quality of the digested pulp product exiting the pulp digester (e.g. a Kappa value) and the residual alkali level are maintained within acceptable target ranges by first determining the error state of the processor and then making prescribed changes to the input process variables depending on the bifurcated assessment of the error states for the two reactant properties (e.g. the blow Kappa and the residual alkali errors).

As shown in FIG. 2, a control 80 receiving error measurements from target values of the resultant properties of the processor and the measured values (i.e. the blow Kappa number and the residual alkali) executes control of the digester by adjusting the input H-factor and alkali dosage. In one embodiment of the present invention, the control includes dead-time compensators which assess the state of the processor about an estimated or predetermined dead time in which an expected change to the output properties, such as for example residual alkali and/or blow Kappa, is anticipated to occur. According to the present invention, other configurations and other control parameters can equally be used according the present invention to permit control of the digester and other processors. Regardless, the control of the present invention utilizes a tunable time "window" to see if the system in responding to control parameter changes are realized.

Figure 3:
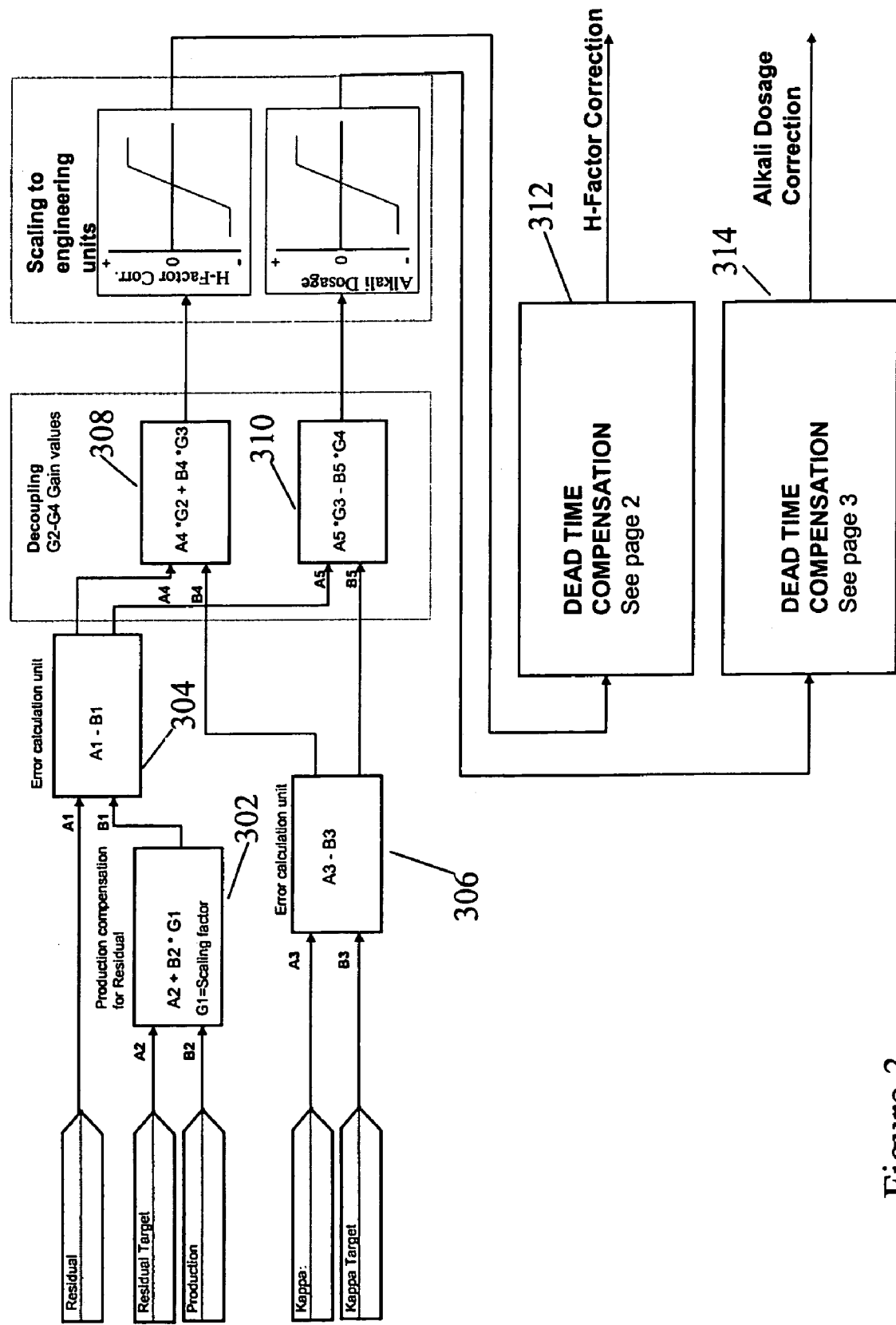
FIG. 3 is an illustrative schematic of a controller of the present invention.
Figure 4:
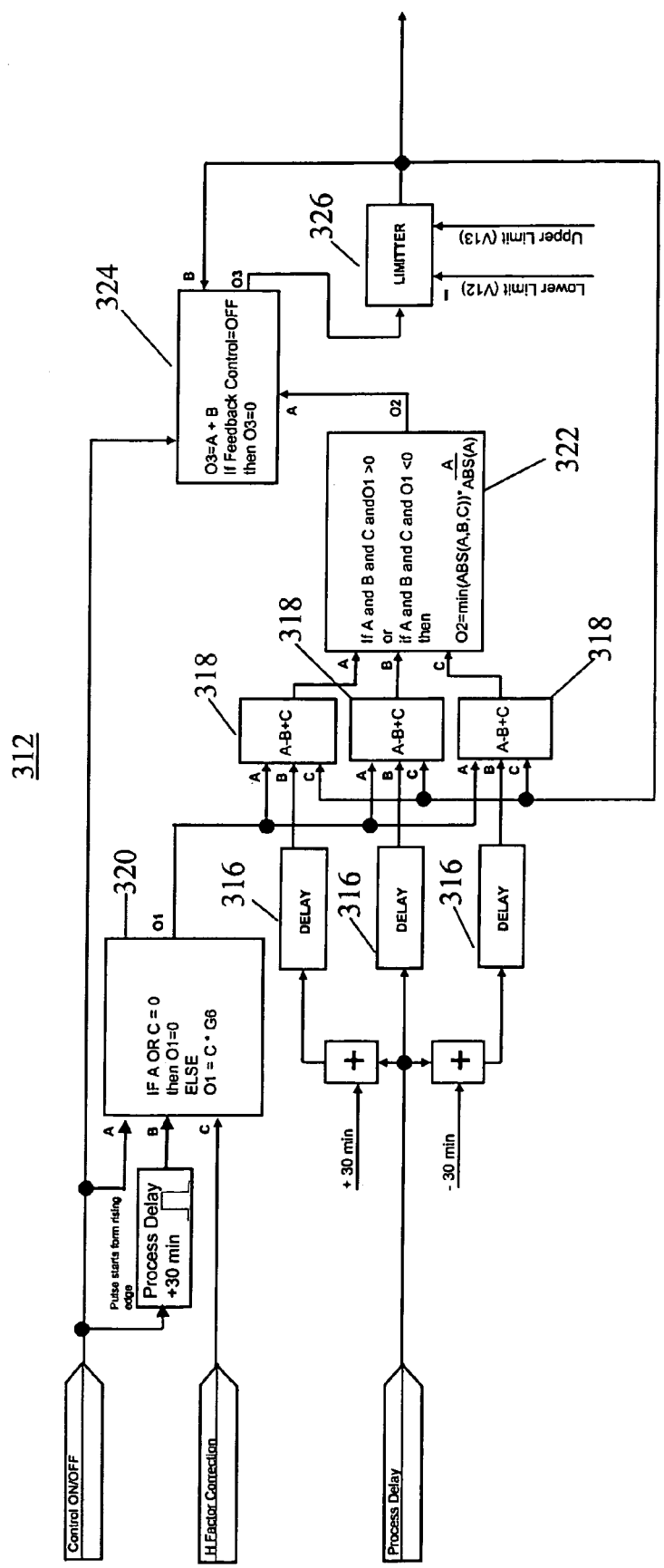
FIG. 4 is an illustrative schematic of a dead-time compensator of the present invention executing control of a digester H-factor.
Figure 5:
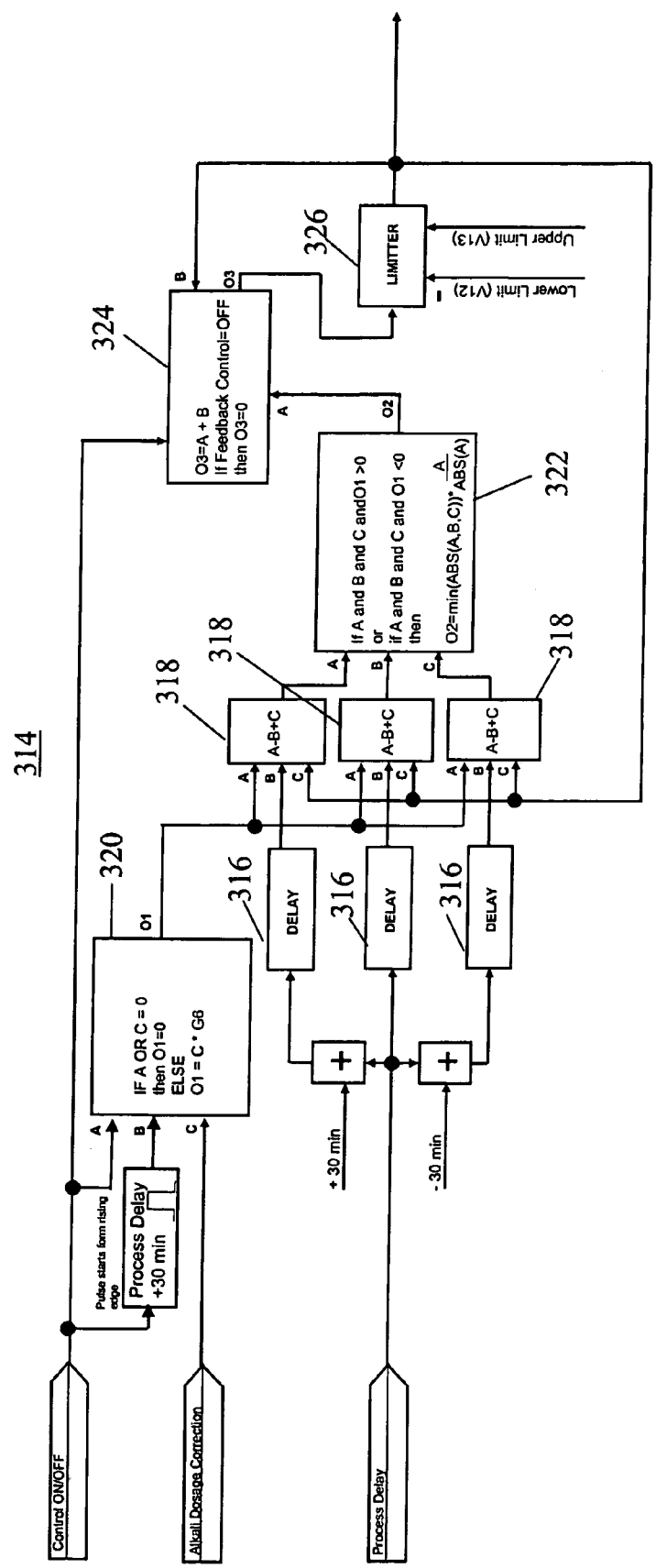
FIG. 5 is an illustrative schematic of a dead-time compensator of the present invention executing control of alkalinity dosage.

FIG. 3–FIG. 5 depict a controller of the present invention as applied in an illustrative example to a digester. Control of the digester is predicated on maintaining targeted levels of, for example, the residual alkali and the blow Kappa level. Furthermore, control of the digester is predicated on maintaining a requisite production level. Thus, as shown by illustration in FIG. 3, inputs to the controller 80 include a measured residual alkali concentration sampled for example in the discharge section 50, a residual alkali concentration target value, a requisite production level, a Kappa level measured in for example the discharge section 50, and a target Kappa level. As shown for the purposes of illustration, a compensator 302 sums through an arbitrary scale factor a requisite production level B2 (adjusted by the arbitrary scale factor G1) and the residual alkali concentration value A2, and outputs the summation as B1. A comparator 304 computes an error difference A1−B1 where A1 is residual alkali concentration taken for example from the discharge section 50. As shown in FIG. 3, comparator 306 computes a difference (i.e., an error) between the measured Kappa level A3 (taken for example from the blow line section 50) and the target Kappa level B3 to output a difference as either error differences B4 or B5.

Error differences from the comparators 304 and 305 are provided to decoupling compensators 308 and 310. As shown in FIG. 3, gain factors G2, G3, and G4 are used in decoupling compensators 308 and 310 to provide weighted summations used to predict a correction to the digester input. The weighted summations can use, for example, linear interpolations of the rule base shown in Table 2 to produce an H-factor correction or an alkali dosage correction scaled to engineering units. Other statistical processes known in the art can be used in the weighted summations. The predicted corrections (i.e., the H-factor correction and the alkali dosage correction) are feed separately to dead-time compensators 312 and 314, respectively.

FIGS. 4 and 5, respectively, illustrate exemplary dead-time compensators 312 and 314 of the present invention. As the details of the dead-time compensators 312 and 314 are similar, for brevity, only a detailed description of the dead-time compensator 312 will be discussed. However, similar functions are performed by the dead-time compensator 314, as illustrated by the similarities between FIGS. 4 and 5.

As shown in FIG. 4, input from the decoupling comparator 308 is fed as one input into the dead-time compensator 312. This input depicted here is an H-factor correction. Additionally, the dead-time compensator 312 receives a control on/off signal and a process delay signal. Due to the large chemical inertia of the pulp digester and the variations in input pulp such as moisture content and lignin concentration, a controller for a processor in one embodiment of the present invention utilizes delay circuits 316 and corresponding comparators 318 to determine if a change to an input parameter, such as for example a H-factor correction or an alkaline dosage concentration correction, have indeed resulted in at least one of the resultant properties of the digested pulp product having changed to acceptable levels. Without the delay circuits 316 and corresponding comparators 318, a controller would at an estimated and/or predetermined time evaluate the state of the digester, and at that time would act on the measured value of the digested product to re-adjust (i.e., control) the digester.

As discussed, measurements taken at that time could be either premature as the expected change has not yet impacted the digested products, or could be belated as the expected change occurred and thereafter dissipated. Either way, a control response without the delay circuits 316 and corresponding comparators 318 of the present invention is non-optimum in that errors derived at the determined dead time do not accurately depict the system response. The delay circuits 316 and the corresponding comparators 318 of the present invention avoid this problem by setting a time-offset (i.e. a delay offset) about the expected dead time in which the "change" should manifest itself. The controller utilizes output from the corresponding comparators 318 to analyze if the change is occurring or has occurred.

For example, as shown in FIG. 4, a process delay such as for example 2.0 hr is input to a delay circuit 316. The delay circuit 316 generates a time offset of 30 min from the 2.0 hr process delay. The time offset value is adjustable and set by the controller. One comparator 318 begins analysis of the properties of the digested pulp product based on the time offset value at 1.5 hr. Another comparator 318 begins analysis of the properties of the digested pulp product at 2.0 hr. Still another comparator 318 begins analysis of the properties of the digested pulp product at 2.5 hr. The comparators 318, as shown in FIG. 4, also receive an input of the H-factor correction. However, as illustrated by example in FIG. 4, the input of the H-factor first passes by a conditional switch 320. The conditional switch 320 decides, based on the value of the process delay and whether or not the digester control has been activated, whether or not to pass the value of the H-factor correction to the comparators 318. For example, if the reactor has just started to warm-up, control may not yet have been activated.

As shown in FIG. 4, outputs of the comparators 318 are compared by a process evaluator 322 such that process evaluator 322 outputs, when all the comparators agree on a directional change for the H-factor (i.e., all the comparators indicate that a positive or a negative change is necessary), a minimum change to the H-factor. Finally, in a preferred embodiment, output from the process evaluator 322 is feed to a verifier 324 which makes sure that the process control is still in an active state, and then to a limiter 326 which compares the output change for the H-factor to make sure that the predicted change for the H-factor is within bounds for prescribed changes to the H-factor.

Thus, the rule-base shown for example in Table 2 can be utilized by the decoupling compensators 308 and 310 to determine for example a scaled (i.e., proportionate) response to error deviations between existing properties such as for example between the blow Kappa number and a target Kappa number or between the residual alkali concentration and a target residual alkali concentration. In one embodiment, the rule-base prescribes an H-factor response or an alkaline dosage response based on the above-noted error states to meet these target values. In another embodiment, the decoupling compensators utilize a model base response such as described in Beller et al. Regardless, a response to the digester, in a preferred embodiment of the present invention, is qualified by evaluating at a multiplicity of subsequent time intervals a response of the digester to a change in H-factor or alkali dosage (i.e. a change in process parameters), before further control (i.e., further adjustments of the H-factor correction or the alkaline dosage concentration) is warranted.

Thus, unlike conventional controllers, a controller of the present invention uses the aforementioned dead-time compensators to assess resultant changes to a processor before taking subsequent changes to the processing parameters. The evaluators in the dead-time compensators of the present invention provide a mechanism by which subsequent process changes (as for example might be warranted in simple proportionate control), subsequent rule changes (as for example might be warranted in an adaptive control) or subsequent model changes (as for example might be warranted in a model-based control) can be evaluated to ascertain if an expected change has occurred.

Figure 6:
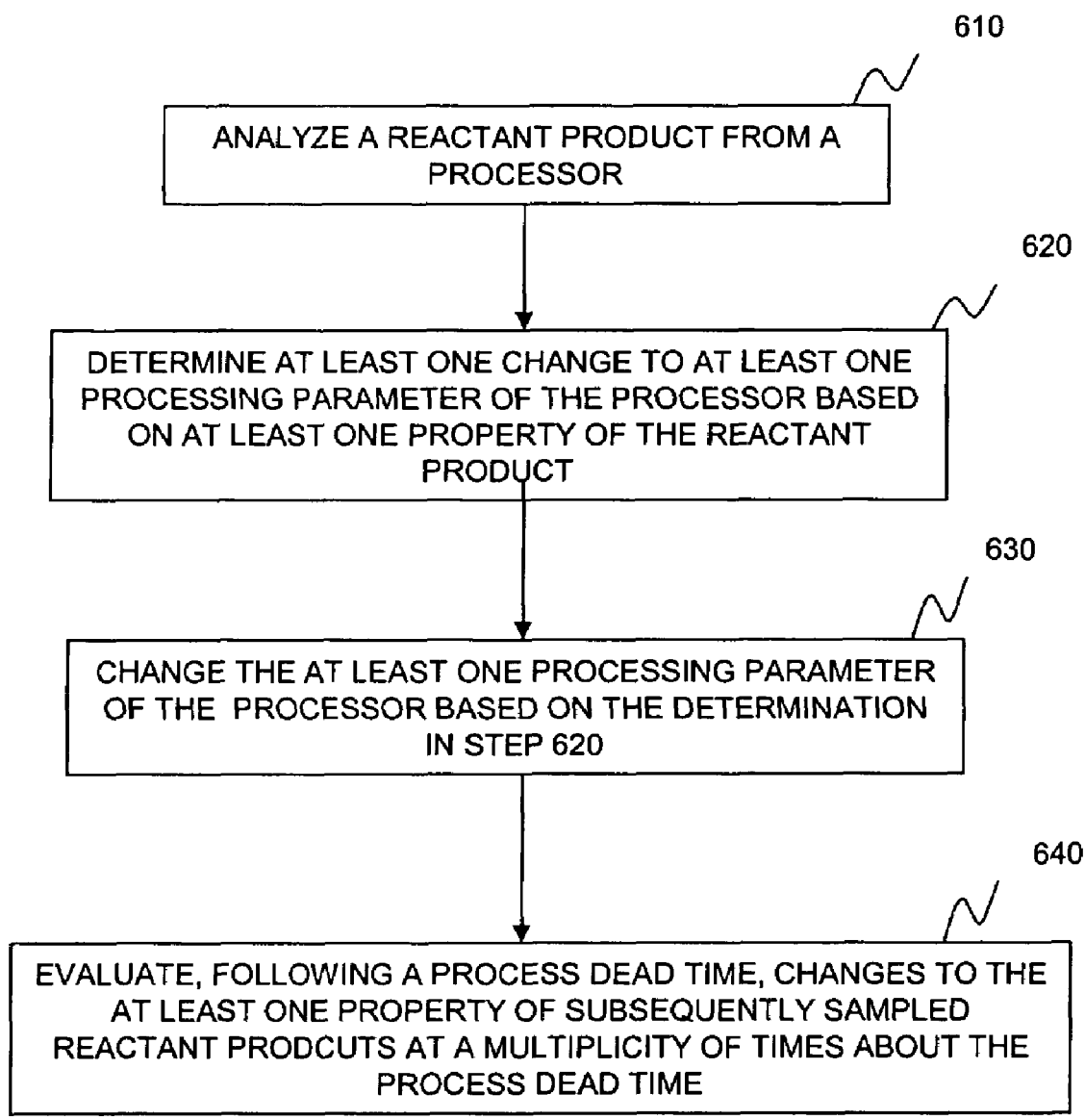
FIG. 6 is a flowchart depicting one method of the present invention.

Thus, in general, the present invention includes a system and a method for control of a processor. The apparatus and methods of the present invention can follow the illustrative steps depicted in FIG. 6. At step 610, a reactant product from the processor is analyzed. At step 620, at least one change to at least one processing parameter of the processor is determined based on at least one property of the reactant product. At step 630, the at least one processing parameter of the processor is changed. At step 640, following a prescribed process dead time, changes to the at least one property of subsequently sampled reactant products are evaluated at a multiplicity of times about the prescribed process dead time. Steps 620–640 and other similar process control steps can be repeated during processor control.

Step 610 can evaluate a reactor process susceptible to disturbances in plug flow conditions. Disturbances can be due to channeling whereby a reactant product prematurely flows into subsequent stages of the processor. Step 610 can analyze the reactant product from any of one of a pulp digester and other paper mill processors such as for example the above-noted oxygen delignifcation processors, the bleaching processors, and the causticizers. At step 610, analysis can be made on a reactant product taken from for example different stages such as for example the sequential cooking sections 10, 20, 30, and 40 and from the discharge section 50 of the pulp digester. Analysis at step 610 can determine a Kappa number, a residual alkali, or any other useful metric of a reactant product. The analysis is preferably performed automatically, but if need be, can be performed off-line and subsequently entered.

Step 620 can determine a prescribed change to the at least one processing parameter based on for example the rule base shown in Table 2. The prescribed changes, however, can be determined from a model base. Further, if the digester is in, for example a warm-up or shut down stage, the determination of a prescribed change can be nullified.

Step 630 can change the at least one processing parameter in a step-change or by a ramped or progressive change to the processing parameters. Preferably, the time to implement the change should be small compared to the anticipated dead time. Step 630 can change at least one processing parameter based on at least a bifurcated error state of the at least two properties of the reactant product.

Step 630 can for example maintain at least one of a Kappa number representative of a cellulose fiber concentration and an alkalinity of the digested pulp product within target values, and can control an H-factor of the digester and at least one of an input alkali dosage concentration and an alkali/wood-input ratio to the digester. Step 630 cancan increase at least one of the H-factor, the input alkali dosage concentration, and the alkali/wood-input ratio when the Kappa number is above a target value, and can decrease at least one of the H-factor, the input alkali dosage concentration, and the alkali/wood-input ratio when the Kappa number of the digested pulp product is below a target value. Step 630 can for example, when a residual alkalinity of the digested pulp product is below a target value, either increase the input alkali dosage concentration or the alkali/wood-input ratio or decrease the H-factor. Step 630 can for example, when a residual alkalinity of the digested pulp product is above a target value, either decrease the input alkali dosage concentration or the alkali/wood-input ratio anor increase the H-factor.

Step 640 can evaluate the changes to the at least one property at a multiplicity of times about an expected deadtime. In an illustrative embodiment described herein, three times were evaluated, but any other number of evaluation times such as for example (2, 4, 5, . . . ) is possible. At step 640, measured values of the at least one property of the reactant product, are compared. By comparison, an assessment is made as to whether or not the prescribed changes have occurred, have not occurred, or are occurring.

Figure 7:
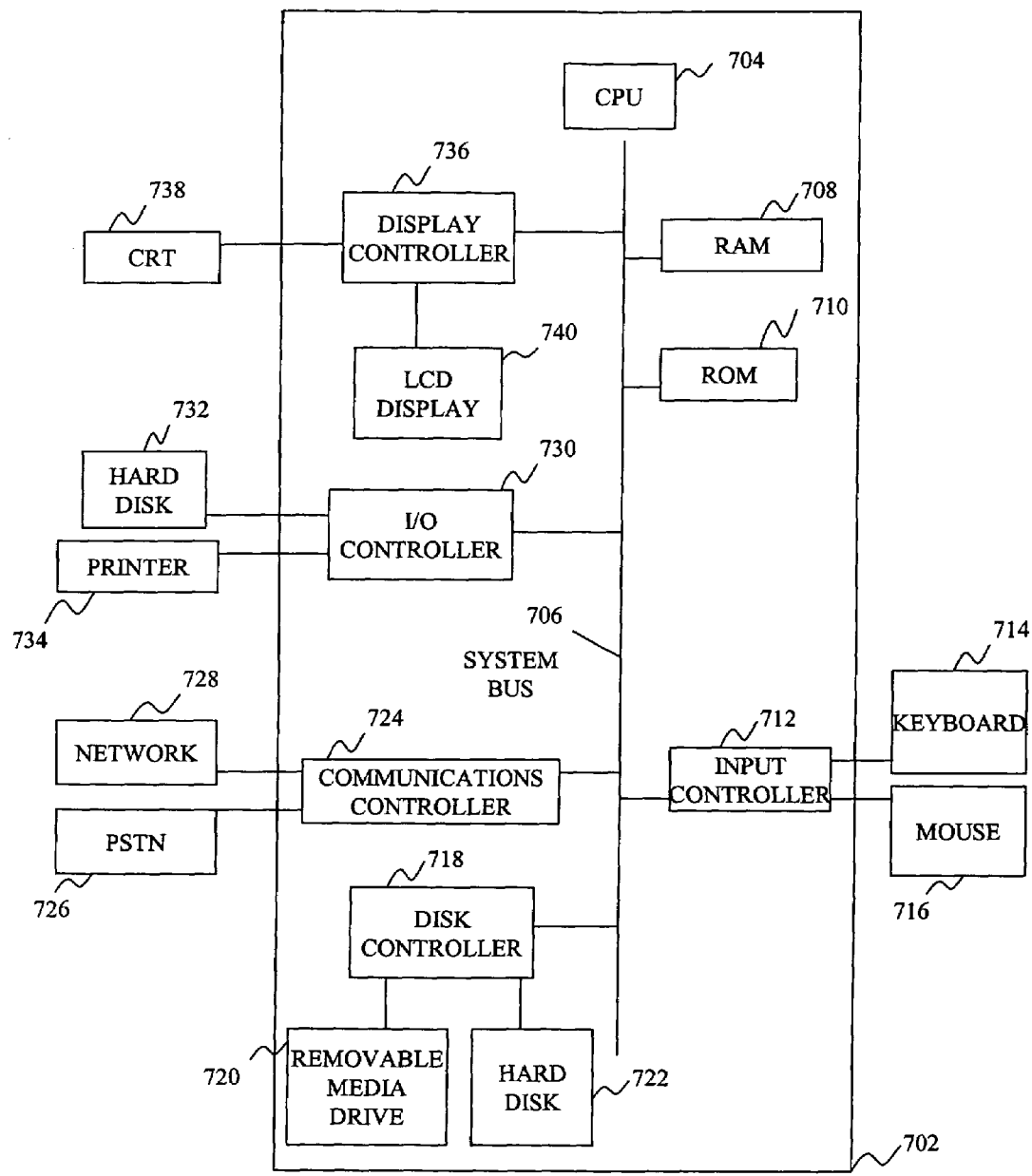
FIG. 7 is a systematic representation of a general purpose computer configured to execute the computer program components of the present invention.

FIG. 7 is a schematic of an illustrative computer 702 of the present invention executing any of the above noted steps. Indeed, the controller 80 of the present invention can include well-known computers such for example a personal computer, a portable computer, a computer workstation with sufficient memory and processing capability, or any device configured to work like a computer. The computer would include a central processing unit 704 (CPU) that communicates with a number of other devices by way of a system bus 706. The computer 702 includes a random access memory (RAM) 708 that stores temporary values used in implementing the process control steps for the controller of the present invention. FIG. 8 is a depiction of bifurcated control data according to one aspect of the invention stored for example in the RAM 708 or any of the other memory units described below permitting the steps described above to the executed.

The central processing unit 704 can be configured for high volume data transmission for performing a significant number of mathematical calculations in controlling the mass spectrometer of the present invention. A Pentium III microprocessor such as the 1 GHz Pentium III manufactured by Intel Inc. may be used for CPU 704. The processor employs a 32-bit architecture. Other suitable processors include but are not limited to the Motorola 500 MHZ Power PC G4 processor and the Advanced Micro Devices 1 GHz AMD Athlon processor. Multiple processors and workstations may be used as well.

A ROM 710 is preferably included in a semiconductor form although other read only memory forms including optical medium may be used to host application software and temporary results. The ROM 710 connects to the system bus 706 for use by the CPU 704. The ROM 710 includes computer readable instructions that, when executed by the CPU 704, perform different functions associated with controlling the mass spectrometer of the present invention. An input control 712 connects to the system bus 706 and provides an interface with various peripheral equipment including a keyboard 714 and a pointing device such as a mouse 716 settles to permit user interaction with graphical user interfaces. The input controller 712 may include different ports such as a mouse port in the form of a PS2 port or, for example, a universal serial bus (USB) port. The keyboard port for the input controller 712 can be in the form of a mini-DIN port although other connectors may be used as well. The input controller 712 may also include serial ports or parallel ports as well.

A disc controller 718 connects via driving cables to a removal media drive 720 which may be implemented as a floppy disc drive, as well as a hard disc drive 722 and a CD-ROM drive (not shown). In addition, a PCI expansion slide is provided on a disc controller 718, a motherboard that hosts the CPU 704. An enhanced graphic port expansion slot is provided and provides 3-D graphics with fast access to the main memory. The hard disc 722 may also include a CD drive that may be readable as well as writable. A communication controller 724 provides a connection to a network 728, which can be a local area network, wide area network, a virtual private network (VPN), or an extranet. The communications controller 724 can also provide a connection to a public switched telephone network (PSIN) 726 for providing Internet access. In one embodiment, the networks 728 and 726 and the communication controller 724 are connected by way of a plurality of connections including a cable-modem connection, digital subscriber line (DSL) connection, fiber optic connection, dial-up modem connection, and the like that connects to the communication controller 724.

An input/output controller 730 also provides connections to the external components such as an external hard disc drive 732, a printer 734, for example, by way of an RS 232 port and a bus line. The input/output controller 730 can be connected to measurement systems for determining for example the blow Kappa number and/or the residual alkali concentration.

A display controller 736 interconnects the system bus 706 to a display device, such as a cathode ray tube (CRT) 738. The CRT can be used for display of the digester processing conditions as well as providing information about the operational status of the processor (e.g., digester temperatures at the sequential stages, input pulp feed rate, input alkali rate, output production rate, blow Kappa, and residual alkali.) While a CRT is shown, a variety of display devices may be used such as an LCD (liquid crystal display) 740, or plasma display device. Display device permits displaying of graphical user interfaces.

The present invention thus also includes a computer-program product that may be hosted on a storage medium and include instructions that can be used to program a computer to perform a process in accordance with the present invention. This storage medium can include, but is not limited to, any type of disk including floppy disks, optical disks, CD-ROM, magneto-optical disks, ROMs, RAMs, EPROMs, EEPROMs, Flash Memory, Magnetic or Optical Cards, or any type of media suitable for storing electronic instructions.

This invention may also be conveniently implemented using a conventional general purpose digital computer programmed according to the teachings of the present specification, as will be apparent to those skilled in the computer art. Appropriate software coding can readily be prepared by skilled programmers based on the teachings of the present disclosure as will be apparent to those skilled in the software art. In particular, the computer program product controlling the operation of the processor of the present invention can be written in a number of computer languages including but not limited to C, C++, Fortran, and Basic, as would be recognized by those of ordinary skill in the art. The invention may also be implemented by the preparation of applications specific integrated circuits or by interconnecting an appropriate network of conventional component circuits, as will be readily apparent to those skilled in the art.

As such, the present invention includes a computer program product including a first computer program product component for analyzing a reactant product from a processor, a second computer program product component for determining based on at least one property of the reactant product at least one change to at least one processing parameter of the processor, a third computer program product component for changing the at least one processing parameter of the processor, a fourth computer program product component for evaluating following a prescribed process dead time changes to the at least one property of the reactant product, and a fifth computer program product component for re-executing the first through fourth computer program product components.

In addition, the present invention includes a computer program product including a first computer program component for analyzing a reactant product from the processor, a second computer program product for determining based on at least two properties of the reactant product a change to at least one processing parameter of the processor, and a third computer program product for changing the at least one processing parameter based on at least a bifurcated error state of the at least two properties of the reactant product.

Numerous modifications and variations of the present invention are possible in light of the above teachings. It is therefore to be understood that within the scope of the appended claims, the invention may be practiced otherwise than as specifically described herein.

The invention claimed is:

1. A system for controlling a processor, comprising:
at least one sampling port connected to a stage of said processor and configured to sample a reactant product from the processor;
a controller having inputs that provide measurements of the at least one property of the reactant product and that provide a target value for the at least one reactant property;
said controller having error calculation units configured to compare the at least one reactant property to the target value in need to control at least one processing parameter of the processor based on measurements of the at least one property of the reactant product such that changes to the at least one processing parameter maintain-the target value for said at least one property of the reactant product; and
a dead time compensator included in said controller and including a process evaluator configured to evaluate said at least one property to determine if said at least one effect has been realized at a plurality of sequential times offset from a dead time wherein said dead time relates to a time before at least one effect of at least one of said changes to the at least one processing parameter is fully realized in said at least one property of the reactant product,
wherein the dead time compensator comprises:
(i) a plurality of sequential delay circuits connected in parallel and configured to offset said dead time by a fixed time interval,
(ii) a plurality of comparators connected in series to respective ones of the sequential delay circuits and configured to compare, at said dead time and at fixed time intervals from said dead time, responses of the digester to said changes, and
(iii) an evaluator configured to receive outputs from the plurality of comparators and to evaluate if said at least one effect is realized and to output a subsequent change for said at least one processing parameter.

2. The system of claim 1, wherein the processor comprises a processor susceptible to disturbances in plug flow conditions.

3. The system of claim 2, wherein said disturbances in plug flow conditions produce channeling whereby said reactant product prematurely flows into subsequent stages of the processor.

4. The system of claim 1, wherein the processor comprises at least one of a pulp digester, an oxygen delignification processor, a bleaching processor, and a causticizer.

5. The system of claim 1, wherein the processor comprises a digester having sequential cooking stages that progressively digest lignin in a pulp or paper product.

6. The system of claim 5, wherein the controller is configured to maintain at least one of a Kappa number representative of a cellulose fiber concentration and an alkalinity of the digested pulp or paper product within target values.

7. The system of claim 5, wherein the controller is configured to control an H-factor of the digester and an input alkali dosage concentration to the digester, said H-factor derived from a time-integrated rate constant for the pulp or paper product in the digester based on a temperature and a throughput of the digester.

8. The system of claim 5, wherein the dead time compensator is configured to adjust said at least one processing parameter after said delay time has expired.

9. The system of claim 8, wherein said evaluator is configured to compare absolute values of said responses and to output a minimum of the absolute values of said responses as said subsequent change.

10. The system of claim 8, further comprising:
a limiter configured to restrict said subsequent change to a maximum value.

11. The system of claim 1, wherein the controller is configured to control based on a rule-base.

12. The system of claim 11, wherein the rule-base comprises error deviations from the target value of said at least one property and associated processing parameter corrections to said processing parameter.

13. The system of claim 11, wherein the controller is configured to linearly interpolate said processing parameter corrections.

14. The system of claim 11, wherein said rule base includes responses predicated on a bifurcated error state in at least two properties of the reactant product.

15. The system of claim 14, wherein the rule-base defines associated processing parameter corrections to said processing parameter depending on said bifurcated error state.

16. The system of claim 11, wherein said a rule base is derived from a model of the process.

17. The system of claim 16, wherein said controller is configured to revise at least one of a rule-base or a model-base based on said at least one effect evaluated by said dead-time compensator.

18. The system of claim 1, further comprising:
a rule base included in a memory unit of the controller and including error deviations from at least two properties of the reactant product and including associated processing parameter corrections to processing parameters of said processor;

said controller configured to compare a bifurcated error state of the at least two properties of the reactor product from target values of the at least two properties to define changes to the processing parameters in order to maintain said target values for said at least two properties of the reactant product.

19. The system of claim 18, wherein the processor comprises at least one of a pulp digester, an oxygen delignification processor, a bleaching processor, and a causticizer.

20. The system of claim 18, wherein the processor comprises a digester having sequential cooking stages that progressively digest lignin in a pulp or paper product.

21. The system of claim 20, wherein the controller is configured to maintain at least one of a Kappa number representative of a cellulose fiber concentration and an alkalinity of the digested pulp product within said target values.

22. The system of claim 21 wherein the controller is configured to control an H-factor of the digester and at least one of an input alkali dosage concentration and an alkali/wood-input ratio to the digester, said H-factor derived from a time-integrated rate constant for the pulp or paper product in the digester based on a temperature and a throughput of the digester.

23. The system of claim 22, wherein the controller is configured to increase at least one of said H-factor, said input alkali dosage concentration, and said alkali/wood-input ratio when said Kappa number is above a target value.

24. The system of claim 22, wherein the controller is configured to decrease at least one of said H-factor, said input alkali dosage concentration, and said alkali/wood-input ratio when said Kappa number of the digested pulp product is below a target value.

25. The system of claim 22, wherein the controller is configured, when a residual alkalinity of the digested pulp product is below a target value, to increase said input alkali dosage concentration or said alkali/wood-input ratio or decrease said H-factor.

26. The system of claim 22, wherein the controller is configured, when a residual alkalinity of the digested pulp product is above a target value, to decrease said input alkali dosage concentration or said alkali/wood-input ratio or increase said H-factor.

27. The system of claim 20, wherein the digester is configured to control based on the following bifurcated relationship:

| Blow Kappa Error | Residual Alkali Error | H-factor Correction | Alkali Dosage Correction |
|---|---|---|---|
| High | High | ++ | OK |
| High | OK | + | + |
| High | Low | OK | ++ |
| OK | High | + | − |
| OK | OK | OK | OK |
| OK | Low | − | + |
| Low | High | OK | −− |
| Low | OK | − | − |
| Low | Low | −− | OK | where blow Kappa error is representative of an error from an expected cellulose fiber concentration in a discharge section of the digester, residual alkali error is representative of an error from an expected residual alkali concentration, H-factor correction is based on a time-integrated rate constant for the pulp or paper product in the digester based on a temperature and a throughput of the digester, alkali dosage correction is based on a measured addition of alkali to be added to the digester, "+" and "++" indicate an increase and a stronger increase to the corrections, "−" and "−−" indicate a decrease and a stronger decrease to the corrections, "OK" refers to an expected value of the residual alkali concentration or the expected cellulose fiber concentration, "High" refers to deviations above the expected values which are predetermined to exceed process tolerances, and "Low" refers to deviations below the expected values which are predetermined to be below process tolerances.

* * * * *